(12) United States Patent
Larsen et al.

(10) Patent No.: US 8,187,848 B2
(45) Date of Patent: May 29, 2012

(54) METHODS OF PROCESSING ENSILED BIOMASS

(75) Inventors: Jan Larsen, Tommerup (DK); Mai Østergaard Petersen, Kolding (DK)

(73) Assignee: Inbicon A/S, Fredericia (DK)

( * ) Notice: Subject to any disclaimer, the term of this patent is extended or adjusted under 35 U.S.C. 154(b) by 0 days.

(21) Appl. No.: 13/132,926

(22) PCT Filed: Dec. 17, 2009

(86) PCT No.: PCT/IB2009/007790
§ 371 (c)(1),
(2), (4) Date: Jul. 7, 2011

(87) PCT Pub. No.: WO2010/073083
PCT Pub. Date: Jul. 1, 2010

(65) Prior Publication Data
US 2011/0275131 A1    Nov. 10, 2011

Related U.S. Application Data

(60) Provisional application No. 61/139,653, filed on Dec. 22, 2008, provisional application No. 61/223,721, filed on Jul. 8, 2009.

(30) Foreign Application Priority Data

Dec. 22, 2008  (DK) ................................. 2008 01834
Jul. 8, 2009   (DK) ................................. 2009 00837

(51) Int. Cl.
*C12P 7/06*    (2006.01)
(52) U.S. Cl. ...................................................... 435/161
(58) Field of Classification Search .................. 435/161
See application file for complete search history.

(56) References Cited

U.S. PATENT DOCUMENTS
2010/0041116 A1    2/2010   Lewis et al.

FOREIGN PATENT DOCUMENTS
DE          291688 A5      7/1991
WO          WO02/38786 A1  5/2002
WO          WO2008134259 A1 11/2008

OTHER PUBLICATIONS

Chen et al. [Applied Biochemistry and Biotechnology, vol. 143, No. 1, pp. 80-92 (Oct. 2007).*
Chen et al. [Applied Biochemistry and Biotechnology, vol. 142, No. 2, pp. 276-290 (Sep. 2007).*
Thomsen et al. [Applied Biochemistry and Biotechnology, vol. 148, No. 1-3, Mar. 2008, pp. 23-33].*
Abe A et al; "Application of Enzymatic Analysis to the Predicition of Digestible Organic Matter and to the Analysis of the Changes in Nutritive Value of Forages" Grassland Science, vol. 25, No. 3, 1979, pp. 231-240.
Rogalinski et al: "Hyrdolysis of lignocellulosic biomass in water under elevated temperatures and pressures" J. of Supercritical Fluids, 47 (2008), 54-63.
Xu et al: "Feasibility of Hydrothermal Pretreatment on Maize Silage for Bioethanol Productions" Appl Biochem Biotechnol (2010) 162:33-42.
Oleskowicz-Popiel, Piotr, Ensiling e Wet-storage method for lignocellulosic biomass for biothanol production, Biomass and bioenergy, 35 (2011) 2087-92.
Inman et al. Feedstock handling and processing effects on biochemical conversion to biofuels. Biofuels. Bioprod. Bioref. 4:562-573 (2010).
Gao et al: Corn Harvest Strategies for Combined Search and Cellulosic Bioprocessing to Ethanol, Agronomy journal, vol. 103, issue 3, 2011.

* cited by examiner

*Primary Examiner* — Tekchand Saidha
(74) *Attorney, Agent, or Firm* — Robert C. Casad, Jr.

(57) ABSTRACT

The invention relates to methods of processing ensiled biomass for production of bioethanol or other fermentation products and, in particular, to methods that do not require expensive pretreatment (e.g. heat or chemical pretreatment).

14 Claims, 3 Drawing Sheets

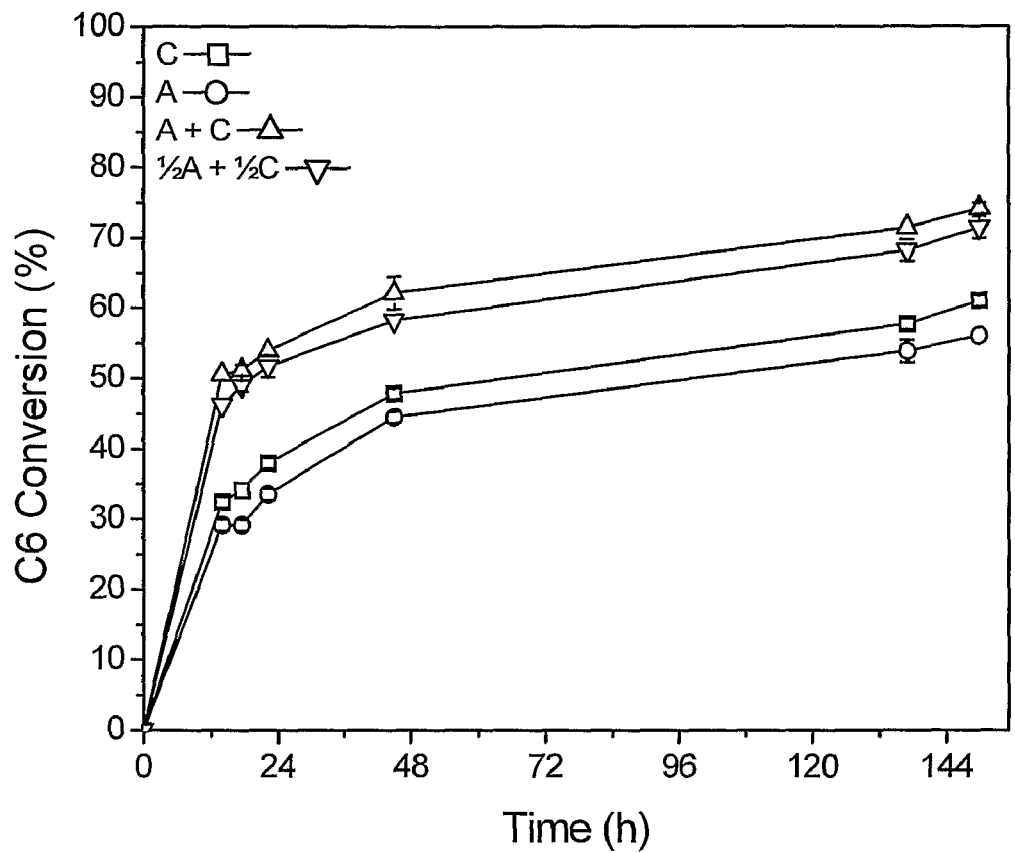
Figure 1: Pre-hydrolysis and SSF of untreated corn silage with four different enzymes/enzyme mixtures.

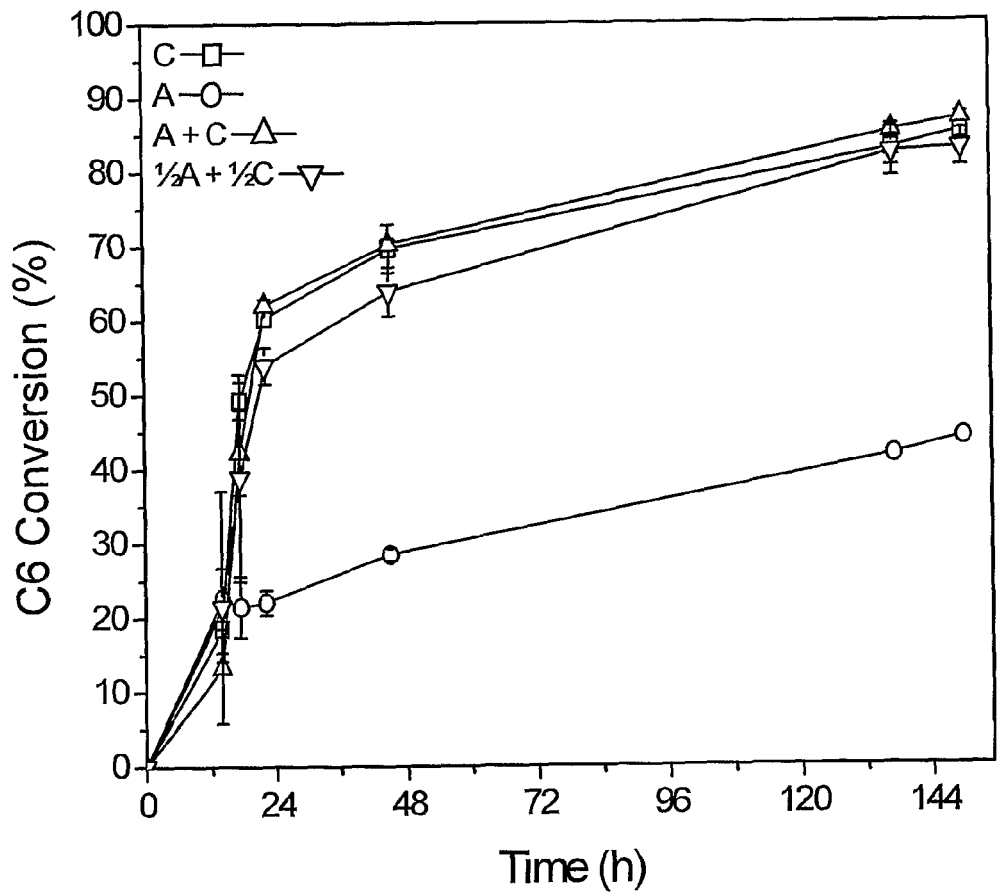
Figure 2: Pre-hydrolysis and SSF of pretreated corn silage with four different enzymes/enzyme mixtures.

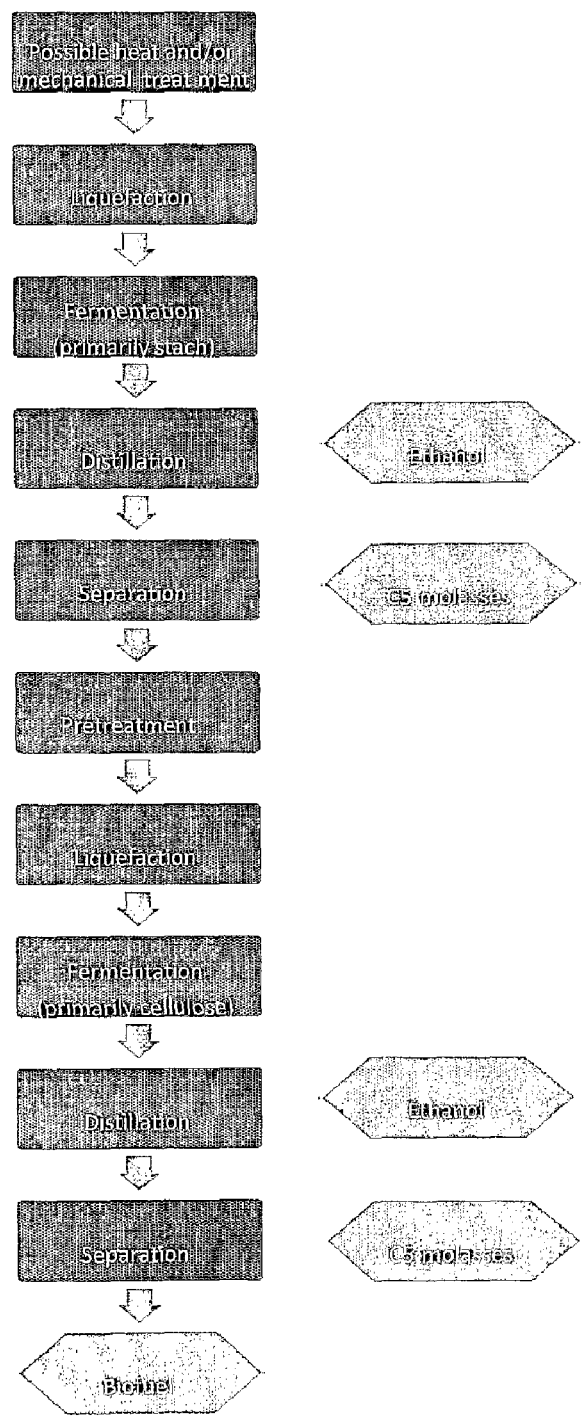
Figure 3. Scheme of ensiled biomass processing.

METHODS OF PROCESSING ENSILED BIOMASS

This application filed Jul. 7, 2011 is a national stage entry of PCT/IB09/07790, international filing date Dec. 17, 2009. PCT/IB09/07790 claims priority from US provisional applications 61/139,653, filed Dec. 22, 2008, and 61/223,721, filed Jul. 8, 2009, and claims foreign priority to DKPA200801834, filed Dec. 22, 2008, and to DKPA200900837, filed Jul. 8, 2009.

FIELD OF THE INVENTION

The invention relates, in general, to methods of processing ensiled biomass for production of bioethanol or other fermentation products and, in particular, to methods that do not require expensive pretreatment (e.g. heat or chemical pretreatment).

BACKGROUND

Bioethanol offers a promising alternative to fossil fuels, providing renewable and "carbon neutral" energy sources that do not contribute to the green house effect. Amongst other possible sources of bioethanol precursors, lignocellulosic biomass can be enzymatically hydrolysed to provide fermentable sugars. However, because of its complex chemical structure, lignocellulose can only be efficiently hydrolysed by presently known enzyme activities after some pretreatment that renders cellulose fibres accessible to enzyme catalysis. Such pretreatment processes typically involve heating biomass to high temperatures (100-250° C.) or addition of chemicals. Large scale production of bioethanol, or other fermentation products, from lignocellulosic biomass requires large scale pretreatment and processing. Accordingly, an intense interest has arisen in methods of biomass processing that reduce costs or otherwise increase commercial viability of bioethanol on a production scale.

Two factors which heavily influence the overall production costs of lignocellulosic bioethanol are pretreatment and the cost of cellulase enzymes. Accordingly, it is advantageous to provide processing methods which reduce energy costs and hydrolysis methods that improve cellulase efficiency.

Ensiled biomass has recently been reported to provide promising raw material for bioethanol production. Silage is primarily used as a method for preservation of plant material as animal feed. Silage typically comprises a whole harvested crop, including stems, leaves and starch-rich grains, which are cut, compressed and stored anaerobically in e.g. silos. The growth of naturally occurring microorganisms during the early stages of ensiling depletes oxygen and converts soluble sugars into acids, thus lowering the pH. After about approximately 3-5 weeks the pH and the concentrations of lactic acid are constant in the ensiling biomass and the silage can be stored until use. Ensiling inhibits unwanted growth of other microorganisms, which decompose polysaccharides, and degrade holocellulose.

Ensiled biomass comprises both starch content, which can be degraded by comparatively inexpensive amylase enzymes, as well as lignocellulosic content, which can be degraded only by cellulase enzymes.

Here we report, surprisingly, that reasonable ethanol yields can be obtained from ensiled biomass that has been hydrolysed by direct enzymatic treatment without energy-consuming pretreatment. Unhydrolysed components of the ensiled biomass can be recovered from the initial enzymatic hydrolysis and/or SSF and subsequently subject to heat pretreatment.

SUMMARY

Provided are energy- and cost-saving methods of processing ensiled biomass in bioethanol production. Ensiled biomass is subject to direct enzymatic hydrolysis, without pretreatment, using amylase enzymes and, optionally, a combination of amylase and cellulase activities. Unhydrolysed components of the ensiled biomass can be recovered from the initial enzymatic treatment and subsequently subject to heat pretreatment.

BRIEF DESCRIPTION OF THE DRAWINGS

FIG. 1 shows percentage conversion of glucan in enzymatic treatment and SSF of ensiled biomass without heat pretreatment. Percentage conversion is shown during prehydrolysis and SSF of untreated corn silage with four different enzymes/enzyme mixtures: 3.5 g/kg amylase (A), 7 FPU/g DM cellulose (C), 7 FPU/g DM cellulose and 3.5 g/kg amylase (A+C) and half-doses of amylase and cellulase, 1.75 g/kg amylase and 3.5 FPU/g DM cellulase (½ A+½ C).

FIG. 2 shows percentage conversion of glucan in enzymatic treatment and SSF of ensiled biomass subject to prior heat pretreatment. Percentage conversion is shown during prehydrolysis and SSF of pretreated corn silage with four different enzymes/enzyme mixtures: 3.5 g/kg amylase (A), 7 FPU/g DM cellulose (C), 7 FPU/g DM cellulose and 3.5 g/kg amylase (A+C) and half-doses of amylase and cellulase, 1.75 g/kg amylase and 3.5 FPU/g DM cellulase (½ A+½ C).

FIG. 3 shows a scheme for processing ensiled biomass.

DETAILED DESCRIPTION OF PREFERRED EMBODIMENTS

As used herein, the following terms have the following meanings:

(i). Ensiled Lignocellulosic Biomass.

Ensiled lignocellulosic biomass refers to whole crops, or substantially whole crops, including any mixture of stems, stalks, and/or leaves and starch-rich grains in which overall carbohydrate content includes a substantial component of cellulose and hemicellulose and in which overall lignin content is 5% or more. The biomass is "ensiled" by storage for a period of at least three weeks under anaerobic conditions.

(ii). Enzymatic Hydrolysis.

Enzymatic hydrolysis refers to treatment of a lignocellulosic biomass with enzyme activities in such manner as to convert cellulose and or starch content to sugars. Enzymatic hydrolysis may be performed using amylases, cellulases, other enzymes or mixtures thereof.

(iii). Pretreatment.

Pretreatment refers to a manipulation of lignocellulosic biomass that renders its cellulosic component more accessible to enzymes that convert carbohydrate polymers into fermentable sugars. Pretreatment may be either heat or chemical pretreatment. Heat pretreatment refers to a pretreatment in which biomass is heated to temperatures of 100° C. or more. Chemical pretreatment refers to a pretreatment that exposes lignocellulosic biomass to added chemicals such as acids or bases to at least a severity comparable to that achieved by heating to 100° C. for 10 minutes. The term "prior to any pretreatment" refers only to sequence of processing steps and does not preclude subsequent pretreatment. Pretreatment does not refer to ensiling, itself, or to any preservatives, bacteria, enzymes or other additives introduced to biomass at the time of ensiling.

(iv). Amylase Enzyme.

An amylase enzyme refers to any enzyme preparation that comprises an activity of α-amylase (1,4-α-D-glucan glucanohydrolase, EC 3.2.1.1). An enzyme preparation that further comprises any combination of β-amylase (1,4-α-D-glucan maltohydrolase, EC 3.2.1.2) and/or γ-amylase (Glucan 1,4-α-glucosidase or "glucoamylase," EC 3.2.1.3) may be "an amylase enzyme" as used herein. An enzyme preparation that is primarily enriched in other enzyme activities, such as cellulase activity, may comprise a significant side activity of amylase and accordingly be an amylase enzyme as used herein.

(v). Cellulase Enzyme.

The term "cellulase enzyme" refers to any one or more "cellulolytic enzymes" in general, including endo-β-1,4-glucanases, that hydrolyse internal bonds in the cellulose polymer, disrupt the crystalline structure and release individual cellulose chains, exo-β-1,4-glucanases (cellobiohydrolases) that hydrolyze cellulose possessively from each end and release oligomers with a chain length of 2-4 sugar moieties. The general term "cellulase" also refers to β-glucosidase (cellobiose) that hydrolyses the products from cellobiohydrolases into D-glucose.

(vi). Effective Amount.

An amount of amylase enzyme is an "effective amount" which, under conditions suitable for amylase enzymatic hydrolysis, would provide conversion within 24 hours of at least 15% of glucan content of ensiled lignocellulosic biomass. A mixture of different amylase enzyme preparations may collectively comprise an "effective amount. An "effective amount" of at least one amylase enzyme may be used in combination with one or more cellulase or other enzyme activities. A very effective amount would provide conversion of at least 20% of glucan content of ensiled lignocellulosic biomass within 24 hours. A super effective amount would provide conversion of at least 25% of glucan content of ensiled lignocellulosic biomass within 24 hours.

(vii). Dry Matter.

Dry matter refers to insoluble material. Dry matter content of biomass refers to intrinsic properties of the biomass. Final dry matter content refers to the insoluble solids content of a hydrolysis and/or SSF reaction mixture at the initiation of hydrolysis.

Methods for production of bioethanol from ensiled lignocellulosic biomass have been described previously. See [1] which is hereby incorporated by reference in entirety. Previously, heat pretreatment was identified as necessary for optimization of ethanol yields from ensiled biomass.

We have discovered that, surprisingly, the starch content of ensiled lignocellulosic biomass is essentially fully accessible to amylase hydrolysis, without requirement for pretreatment. Avoiding pretreatment is actually preferable. By avoiding starch losses normally incurred during pretreatment, ultimate yields of fermentable sugars from starch content are improved.

We have further discovered that a surprisingly high portion of the cellulosic content of ensiled lignocellulosic biomass is accessible to cellulase hydrolysis, without requirement for pretreatment.

Accordingly, some embodiments of the invention provide methods of processing ensiled biomass in bioethanol production that do not require energy- and/or cost-consuming pretreatment.

Some embodiments provide a method of processing ensiled lignocellulosic biomass comprising providing an ensiled lignocellulosic biomass, and
subjecting said ensiled biomass to enzymatic hydrolysis using an effective amount of at least one amylase enzyme in combination with one or more cellulase enzymes prior to any pretreatment.

In preferred embodiments, enzymatic hydrolysis is conducted in whole or in part as a simultaneous saccharification and fermentation (SSF) process.

Still other embodiments provide the further steps of
recovering unhydrolysed material from the ensiled biomass after enzymatic hydrolysis, and
subjecting said unhydrolysed material to heat pretreatment between 110-250° C.

Any suitable feed stock may be used to practice methods of the invention, including alfalfa, grasses, empty fruit baskets, legumes, corn, sugar cane, sorghum, rye, wheat, barley, triticale, rice and other plants. Preferred feedstocks have a glucan content (that is, combined starch and cellulose content) of at least 40%, most preferably at least 50%. The glucan content of preferred feedstocks comprises at least 30% starch, more preferably at least 40% starch, or still more preferably at least 50% starch.

In preferred embodiments, prior to ensiling, biomass will have been pre-processed by mechanical or other means including but not limited to chopping, cutting, milling, slicing or any suitable method of portioning the biomass and reducing particle size. Ensiled biomass may be stored on field, in a silo, in any suitable enclosure or in any way which substantially hinders unwanted microbial degradation of the biomass. In preferred embodiments, biomass is ensiled for at least five weeks. In some embodiments, biomass can be harvested at an optimal stage of maturity and ensiled using any of the methods known in the art, including but not limited to the methods described in [2] and/or [3], which are hereby incorporated by reference in entirety.

In preferred embodiments, production-scale quantities of suitable ensiled biomass will be used to practice methods of the invention. Preferably, methods of the invention are practiced using at least 500 kg; more preferably, at least 1,000 kg ensiled biomass; more preferably, at least 5,000 kg; still more preferably, at least 10,000 kg ensiled biomass.

The dry matter content of suitable ensiled biomass can be above 20%, or still more preferably above 30%.

Any suitable amylase may be used to practice embodiments of the invention. In preferred embodiments, enzyme preparations are used that comprise a mixture of α-amylase and γ-amylase.

Suitable preparations enriched in α-amylase may include commercial preparations including NS50033™, Novozymes. Alternatively, α-amylase may be prepared by methods well known in the art from microorganisms including thermophilic *Bacillus* strains in general, *B. Subtilis, B. Amyloliquefaciens, Trichoderma* strains, *Aspergillus fumigatus*, and other suitable sources.

Suitable conditions for enzymatic hydrolysis are generally well known for any given enzyme preparation comprising at least one amylase. Amylase preparations may be supplemented with some quantities of cellulase preparations to improve yields. In preferred embodiments, enzymatic hydrolysis is conducted as a pre-hydrolysis prior to simultaneous saccharification and fermentation (SSF). Pre-hydrolysis is preferably conducted for at least 6 hours under suitable conditions. Alternatively, prior to fermentation, ensiled biomass may be as fully hydrolysed as is permitted by enzymatic treatment prior to any pretreatment. After hydrolysis, or pre-hydrolysis, the hydrolysed component can be separated and fermented. Unhydrolysed material can subsequently be removed and subject to heat-pretreatment followed by additional enzymatic hydrolysis, primarily using cellulase preparations. Alternatively, unhydrolysed material can be removed after SSF and subsequently subject to heat-pretreatment followed by additional enzymatic hydrolysis with cellulase preparations.

Example 1

Enzymatic Treatment and SSF of Ensiled Biomass without Pre-Treatment

Whole corn from Nørupgård, Denmark, was harvested in October, 2007, chopped in a harvester, thoroughly compressed, and stored under anaerobic conditions without addition of chemicals in a bunker silo until April, 2008. Dry matter content of the silage was approximately 31%.

The composition of untreated corn silage was determined according to the NREL standard "Determination of lignin and structural carbohydrates in biomass:"

| Composition of corn ensilage (% of dry matter) | | | | | |
|---|---|---|---|---|---|
| | Glucan | Xylan | Arabian | Lignin | Ash | Residual |
| Not treated | 56.22 | 13.78 | 4.10 | 10.11 | 4.06 | 11.72 |

"Glucan" refers to the composition of both starch and cellulose.

Prior to enzymatic hydrolysis experiments, the silage was dried for 2-3 days (at 40° C.) and milled to avoid experimental errors due to heterogeneity of the material.

Enzymatic hydrolysis of the "untreated" silage (i.e., not subject to heat pre-treatment) was assessed using four different enzyme treatments:
 (C): cellulase at 7 FPU/g DM (combination of CELLUCLAST™ and NOVOZYMES188™, mixed 5:1 by volume);
 (A): amylase at 3.5 g/kg DM (NS50033™, Novozymes);
 (A+C): mixture of amylase and cellulase; cellulase at 7 FPU/g DM (combination of CELLUCLAST™ and NOVOZYMES188™, mixed 5:1 by volume) and amylase at 3.5 g/kg DM (NS50033™, Novozymes); and
 (½A+½C): mixture of amylase and cellulase at half-doses of the individual enzymes; cellulase at 3.5 FPU/g DM (combination of CELLUCLAST™ and NOVOZYMES188™, mixed 5:1 by volume) and amylase at 1.75 g/kg DM (NS50033™, Novozymes).

The conversion of cellulose to ethanol was determined as % conversion calculated from weight loss during SSF and confirmed by HPLC analyses after prehydrolysis and at the end of SSF.

All experiments were performed by diluting the dried and milled corn silage to 5% final dry matter content (insoluble solids) with 0.1 M Na-acetate buffer (pH=5.0) in 60 g total in 100 ml blue cap bottles. CELLUCLAST™ and NOVOZYMES188™ were mixed 5:1 (v/v) and diluted in 0.1 M Na-acetate buffer as was NS50033™ (Novozymes, cold mashing enzyme with an optimum at approximately 50° C.) prior to addition.

All samples were prehydrolysed in a shaking incubator for 6 h at 50° C. and 250 rpm. After 6 h, the bottles were cooled to approximately 33° C. and baker's yeast was added (1 g per kg final dry matter content, THERMOSACC DRY™, Ethanol Technology). SSF was continued for 144 h on a shaking incubator at 33° C. and 250 rpm.

Results for each of the four enzyme treatments are shown in FIG. 1. As shown, enzymatic treatment with amylase alone was sufficient to convert 56% of the glucan content. This indicates that the starch component of silage glucan content is readily accessible to amylase hydrolysis, without pretreatment. Furthermore, these results indicate that the total glucan content was about 31% starch, overall.

Hydrolysis and SSF using only cellulase gives a slightly larger conversion (61%) than amylase alone. This is probably because the cellulases can convert part of the cellulose content and, at the same time, have a substantial amylase side activity. Previous experiments with different types of non-pretreated biomass have shown that 12-25% of the glucan in the materials can be converted into ethanol without pretreatment. When both cellulases and amylases are added at the same time, a glucan conversion of approximately 74% is obtained at full dose and approximately 72% at half-doses of the enzymes.

Example 2

Enzymatic Treatment and SSF of Ensiled Biomass Subject to Prior Heat Pretreatment Whole corn from Nørupgård, Denmark, was harvested in October, 2007, chopped in a harvester, thoroughly compressed, and stored under anaerobic conditions without addition of chemicals in a bunker silo until April, 2008. Dry matter content of the silage was approximately 31%.

Prior to enzymatic hydrolysis experiments, the silage was dried for 2-3 days (at 40° C.) and milled to avoid experimental errors due to heterogeneity of the material.

Milled silage was steam pretreated at 190° C. for 12 minutes.

The composition of the pretreated corn silage was determined according to the NREL standard "Determination of lignin and structural carbohydrates in biomass:"

| Composition of corn ensilage (% of dry matter) | | | | | |
|---|---|---|---|---|---|
| | Glucan | Xylan | Arabian | Lignin | Ash | Residual |
| Pre-treated | 53.32 | 14.24 | 2.36 | 17.68 | 2.93 | 9.46 |

Enzymatic hydrolysis and SSF of the heat pretreated silage was conducted as described for example 1.

Results for each of the four enzyme treatments are shown in FIG. 2. As shown, in experiments with amylase alone the conversion is only about 45%. This indicates that the starch content has been reduced after pretreatment, probably because of degradation during pretreatment or removal of starch as a result of washing out. FIG. 2 furthermore shows that hydrolysis and SSF using cellulase alone results in about 85% conversion, the combination of amylase and cellulose results in about 87% conversion, while using half the enzyme dosages of both cellulase and amylase results in about 83% conversion. This indicates that pretreatment is required for cellulose conversions above 80%. However, depending on pretreatment parameters, this will likely result in some degradation and washing-out of the starch. These experiments indicate that pretreatment of silage is wasteful, since the starch and a part of the cellulose is accessible for enzymatic hydrolysis without pretreatment, and since some of the sugars may be dissolved or degraded during pretreatment. It is clearly advantageous to organize processing of ensiled biomass so that easily accessible sugars are metabolised without pretreatment. After hydrolysis and fermentation at a high final dry matter content, ethanol can be distilled from the fermentation mixture. The solid fraction from distillation can be separated and subsequently pretreated to make the cellulose residue accessible for enzymatic hydrolysis.

Example 3

Theoretical Bioethanol Process Yields Involving Direct Enzymatic Hydrolysis and SSF Followed by Pretreatment of Residual Material FIG. 3 illustrates a scheme for processing ensiled corn silage, or other ensiled biomass, to bioethanol. Silage is first processed without pretreatment by liquefaction at high final dry matter content (insoluble solids) according to the process described by WO2006/056838, which is hereby incorporated by reference in entirety. At high final dry matter content, fermentation and/or SSF can produce ethanol yields of greater than 4% (w/w) in the fermentation broth in a single vessel, without accumulation of process streams over several fermentation batches, as required using low high dry matter hydrolysis and fermentation.

Unpretreated silage is liquefied and fermented (First fermentation). Ethanol is distilled and C5 fraction collected. An insoluble solid fraction is obtained from the distillation mixture which is, then, subject to pretreatment, preferably heat pretreatment. This pretreated, unhydrolysed material is, then, also liquefied and fermented (Second fermentation).

Yields of the process illustrated in FIG. 3 can be calculated from the results presented in Examples 1 and 2:

| | |
|---|---|
| Total glucan content: | 56.22% of DM |
| Starch | App. 56% of glucan |
| Cellulose | App. 44% of glucan |
| Glucan conversion without pretreatment with amylase alone | App. 56% |
| Glucan conversion without pretreatment with amylase and cellulase | App. 70% |
| DM content raw material | App. 31% |
| Glucan conversion with pretreatment with cellulase | App. 85% |

The relationship between final dry matter content of the hydrolysis and/or SSF mixture and final ethanol yield can be readily calculated according to equation 1:

$$\% Et = (1\ kg*(X)*(\%\ glucan)*(\%\ conv)*(1.1)*(theory\ yield))/(1\ kg-(1\ kg*(X)*(\%\ glucan)*(\%\ conv)*(1.1)*(theory\ yield))) \quad \text{Eq. 1:}$$

where
% Et=kg ethanol/kg total
X=kg DM/kg total (i.e, final dry matter content)
% glucan=kg glucan/kg DM
% conv=kg glucan free/kg glucan total
1.1=kg C6 sugar/kg glucan free
Theory yield=0.51 kg ethanol/kg sugar Where the First fermentation utilizes silage hydrolysed by treatment with amylases alone, without significant cellulase activity, only starch will be converted to ethanol. In this case, a final dry matter content of at least 22% is necessary to achieve a final ethanol concentration of at least 4% (w/w):

$$0.04=(1\ kg*(X)*0.56*0.55*1.1*0.51)/(1\ kg-1\ kg*(X)*0.56*0.55*1.1*0.51) \Leftrightarrow X=0.22$$

Where the First fermentation utilizes silage hydrolysed by both amylases and cellulases, a final dry matter content of at least 18% is necessary to achieve ethanol concentration at least 4%:

$$0.04=(1\ kg*(X)*0.56*0.70*1.1*0.51)/(1\ kg-1\ kg*(X)*0.56*0.70*1.1*0.51) \Leftrightarrow X=0.18$$

For the Second fermentation, a glucan loss of 5% and a glucan conversion of 85% are assumed, as reported in Example 2. If only starch is converted during the First Fermentation, then the theoretical glucan (cellulose) content of the fiber residue is (36% of dry matter)*(95% glucan remaining)=34.2% of dry matter. In this case, a final dry matter content of at least 24% is necessary to achieve ethanol concentration at least 4% in the Second fermentation:

$$0.04=(1\ kg*(X)*0.342*0.85*1.1*0.51)/(1\ kg-1\ kg*(X)*0.342*0.85*1.1*0.51) \Leftrightarrow X=0.24$$

Table I shows an estimate of the mass balance for the process described in FIG. 3 where conversion of 56% (amylase alone) or 70% (amylase plus cellulase) is obtained in the First fermentation, followed by hydrolysis and Second fermentation of the reside at 30% final dry matter content. If the corn silage is treated with both amylase and cellulase at 30% final dry matter content and fermented (without water dilution), an ethanol concentration of approx 7.5% can be obtained at a conversion of approximately 70% from both cellulase and amylase treatment. If only amylase is used, an ethanol concentration of approx 6% may be obtained at 56% glucan conversion. After the First fermentation, an unhydrolysed residue of maximum about 600 kg will remain (per tonne of dry matter added to the process) containing approx 160 kg cellulose (at 70% conversion). The residue estimate is a maximum, since some degradation or dissolution of hemicelluloses may occur during the First fermentation. The residue before the Second fermentation will contain minimum 27% cellulose.

If this residue is pretreated (glucan yield of 95% after the pretreatment) and diluted to 30% dry matter, it will be possible to obtain between 4.7 and 6.2% of ethanol at full conversion in the Second fermentation.

TABLE 1

Estimate of the mass balance for the process at 56 and 70% decomposition, respectively, in the first fermentation. Basis for the estimate is 1000 kg dry matter, corresponding to 3100 kg of corn silage.

| | At 56% conversion in the first fermentation | At 70% conversion in the first fermentation |
|---|---|---|
| Ethanol from the first fermentation [kg] | 178 | 222 |
| Ethanol conc. after the first fermentation [w/w-%] | 6.0 | 7.5 |
| Residue dry matter [kg] | 686 | 608 |
| Residue C6 [kg] | 246 | 168 |
| After pretreatment - 95% recovery of C6 | | |
| Residue C6 [kg] | 234 | 160 |
| % of cellulose of the residue [%] | 33 | 27 |
| Diluted to 30% dry matter, hydrolysed and fermented | | |
| Liquid addition [kg] | 1573 | 1400 |
| Ethanol [kg] | 132 | 90 |
| Ethanol conc. after the second fermentation [w/w-%] | 6.2 | 4.7 |

The examples and descriptions above provide representative examples of particular embodiments and are not intended to limit the scope of the invention as defined by the claims.

REFERENCES

1. M. Thomsen et al., "Pretreatment of whole crop harvested, ensiled corn for ethanol production," Appl. Biochem. Biotechnol. (2008) 148(1-3):23.
2. Z. Weinberg and G. Ashbell, "Engineering aspects of ensiling," Biochemical Engineering Journal (2003), 13:18.
3. E. Charmley, "Towards improved silage quality," Canadian Journal of Animal Science (2001), 81(2):157.

The invention claimed is:

1. A method of processing ensiled lignocellulosic biomass comprising
   providing an ensiled whole crop lignocellulosic biomass, and
   subjecting said ensiled biomass to enzymatic hydrolysis prior to any pre-treatment using an effective amount of at least one amylase enzyme, sufficient to provide conversion within 24 hours of at least 15% of glucan content, in combination with one or more cellulase enzymes
   wherein the ensiled biomass is whole crop corn,
   wherein the method is practiced using at least 500 kg ensiled biomass, and
   wherein the enzymatically hydrolysed ensiled biomass is further fermented to ethanol.

2. The method of claim 1 further comprising the steps of
   recovering unhydrolysed material from the hydrolysed biomass, and
   subjecting said unhydrolysed material to heat pre-treatment between 110-250° C.

3. The method of claim 2 further comprising the steps of subjecting said recovered, unhydrolysed, pretreated material to enzymatic hydrolysis and fermentation.

4. The method of claim 1 wherein the amount of the at least one amylase enzyme is a very effective amount sufficient to provide conversion within 24 hours of at least 20% of glucan content.

5. The method of claim 1 wherein the final dry matter content of said ensiled biomass at the start of enzymatic hydrolysis is at least 20%.

6. The method of claim 1 wherein the at least one amylase preparation comprises a mixture of at least α-amylase and γ-amylase.

7. The method of claim 1 wherein enzymatic hydrolysis is conducted as a prehydrolysis followed by simultaneous saccharification and fermentation (SSF).

8. The method of claim 1 wherein glucan conversion after at least 144 hours SSF is at least 55%.

9. The method of claim 1 wherein the amount of the at least one amylase enzyme is a super effective amount sufficient to provide conversion within 24 hours of at least 25% of glucan content.

10. The method of claim 1 wherein fermentation is conducted in whole or in part as a simultaneous saccharification and fermentation (SSF) process.

11. The method of claim 1 wherein prior to ensiling, the biomass was pre-processed by mechanical or other means including any one of chopping, cutting, milling, or slicing.

12. The method of claim 1 wherein the amylase enzyme comprises an α-amylase preparation from any thermophilic *Bacillus* strain, *B. Subtilis, B. Amyloliquefaciens, Trichoderma* strain, or *Aspergillus fumigatus*.

13. The method of claim 1 wherein the biomass was harvested at an optimal stage of maturity.

14. The method of claim 1 wherein the biomass was ensiled on a field or in a silo.

* * * * *